US012742213B2

(12) United States Patent
Xu et al.

(10) Patent No.: US 12,742,213 B2
(45) **Date of Patent: *Sep. 22, 2026**

(54) PROTECTION SEQUENCE, PRIMER, PROBE, COMPOSITION AND KIT FOR STEADY-STATE RAPID DETECTION OF NOVEL CORONAVIRUS, AND USE THEREOF AND METHOD THEREFOR

(71) Applicants: THE EYE HOSPITAL OF WENZHOU MEDICAL UNIVERSITY, Wenzhou City (CN); WENZHOU OJA BIOTECHNOLOGY CO., LTD., Wenzhou City (CN)

(72) Inventors: Tao Xu, Wenzhou City (CN); Jingu Wang, Wenzhou City (CN); Jiangfan Chen, Wenzhou City (CN); Jia Qu, Wenzhou City (CN)

(73) Assignees: The Eye Hospital of Wenzhou Medical University, Wenzhou City (CN); Wenzhou Oja Biotechnology Co., Ltd., Wenzhou City (CN)

( * ) Notice: Subject to any disclaimer, the term of this patent is extended or adjusted under 35 U.S.C. 154(b) by 683 days.

This patent is subject to a terminal disclaimer.

(21) Appl. No.: 18/004,410

(22) PCT Filed: Aug. 31, 2020

(86) PCT No.: PCT/CN2020/112398

§ 371 (c)(1),
(2) Date: Jan. 5, 2023

(87) PCT Pub. No.: WO2021/223349

PCT Pub. Date: Nov. 11, 2021

(65) Prior Publication Data

US 2024/0279752 A1 Aug. 22, 2024

(30) Foreign Application Priority Data

May 6, 2020 (CN) ........................ 202010372408.7

(51) Int. Cl.

*A61K 39/215* (2006.01)
*C12Q 1/6851* (2018.01)
*C12Q 1/70* (2006.01)
*C12Q 1/6806* (2018.01)

(52) U.S. Cl.

CPC ............ *C12Q 1/701* (2013.01); *A61K 39/215* (2013.01); *C12Q 1/6851* (2013.01); *C12Q 1/6806* (2013.01)

(58) Field of Classification Search

None

See application file for complete search history.

(56) References Cited

U.S. PATENT DOCUMENTS

2023/0127238 A1* 4/2023 Kana .................... C12Q 1/6806 435/5

FOREIGN PATENT DOCUMENTS

| CN | 110117644 A | 8/2019 |
|---|---|---|
| CN | 111004870 A | 4/2020 |
| CN | 111020064 A | 4/2020 |
| CN | 111088408 A | 5/2020 |

OTHER PUBLICATIONS

NCBI Reference Sequence NC_045512.2 “Severe acute respiratory syndrome coronavirus 2 isolate Wuhan-Hu-1, complete genome,” National Library of Medicine/National Center for Biotechnology Information, Mar. 30, 2020 (5 pages).

Guo, Yuanyuan, et al., “Comparison and Analysis of the Detection Performance of Six SARS-CoV-2nucleic Acid Detection Reagents,” *Chongqing Medical Journal*, vol. 49, No. 15, pp. 1-11 (Feb. 12, 2020).

Ai, Jing-Wen, et al., “Era of molecular diagnosis for pathogen identification of unexplained pneumonia, lessons to be learned,” *Emerging Microbes & Infections*, vol. 9, No. 1, pp. 597-600 (Mar. 16, 2020).

* cited by examiner

*Primary Examiner* — Benjamin P Blumel

(74) *Attorney, Agent, or Firm* — Christensen, Fonder, Dardi & Busse PLLC; John P. Fonder

(57) ABSTRACT

The present invention uses a lysis protection solution to treat patient samples, and the samples release genes targeting the 2019-nCOV virus. In the lysis protection solution, multiple target genetic loci are effectively identified by a protection sequence to form a compound, making 2019-nCOV RNA more stable and avoiding extracting purified RNA. The enriched 2019-nCOV RNA compound is further subjected to reverse transcription to obtain cDNA. A signal is then amplified for 40 cycles after the product is identified by a specific 2019-nCOV probe.

7 Claims, 4 Drawing Sheets

Specification includes a Sequence Listing.

| | RNASE1 | RNASE2 | RNASE3 | RNASE4 | RNASE5 | RNASE6 | RNASE7 |
|---|---|---|---|---|---|---|---|
| Random Forest | 0.85* | 0.75 | 0.75 | 0.75 | 0.75 | 0.9* | 0.75 |
| SVM | 0.577 | 0.564 | 0.819* | 0.571 | 0.738 | 0.347 | 0.652 |

| | RNASE1 | RNASE2 | RNASE3 | RNASE4 | RNASE5 | RNASE6 | RNASE7 |
|---|---|---|---|---|---|---|---|
| Random Forest | 0.9* | 0.85 | 0.75 | 0.7 | 0.7 | 0.75 | 0.85* |
| SVM | 0.74 | 0.738 | 0.903* | 0.69 | 0.534 | 0.405 | 0.784 |

SEQUENCE LISTING

<160> NUMBER OF SEQ ID NOS: 8

<210> SEQ ID NO 1
<211> LENGTH: 39
<212> TYPE: DNA
<213> ORGANISM: Artificial Sequence
<220> FEATURE:
<223> OTHER INFORMATION: Synthesized Protection Sequence

<400> SEQUENCE: 1
cctcttctcg ttcctcatca cgtagtcgca acagttcaa 39

<210> SEQ ID NO 2
<211> LENGTH: 39
<212> TYPE: DNA
<213> ORGANISM: Artificial Sequence
<220> FEATURE:
<223> OTHER INFORMATION: Synthesized Protection Sequence

<400> SEQUENCE: 2
gtcctcactg ccgtcttgtt gaccaacagt ttgttgact 39

<210> SEQ ID NO 3
<211> LENGTH: 19
<212> TYPE: DNA
<213> ORGANISM: Artificial Sequence
<220> FEATURE:
<223> OTHER INFORMATION: Synthesized Amplification Primer

<400> SEQUENCE: 3
caagcctctt ctcgttcct 19

<210> SEQ ID NO 4
<211> LENGTH: 22
<212> TYPE: DNA
<213> ORGANISM: Artificial Sequence
<220> FEATURE:
<223> OTHER INFORMATION: Synthesized Amplification Primer

<400> SEQUENCE: 4
gcagcagatt tcttagtgac ag 22

-continued

```
<210> SEQ ID NO 5
<211> LENGTH: 19
<212> TYPE: DNA
<213> ORGANISM: Artificial Sequence
<220> FEATURE:
<223> OTHER INFORMATION: Synthesized Amplification Primer

<400> SEQUENCE: 5

gccacttctg ctgctcttc                                             19


<210> SEQ ID NO 6
<211> LENGTH: 20
<212> TYPE: DNA
<213> ORGANISM: Artificial Sequence
<220> FEATURE:
<223> OTHER INFORMATION: Synthesized Amplification Primer

<400> SEQUENCE: 6

tgattgtcct cactgccgtc                                            20


<210> SEQ ID NO 7
<211> LENGTH: 22
<212> TYPE: DNA
<213> ORGANISM: Artificial Sequence
<220> FEATURE:
<223> OTHER INFORMATION: Synthesized Amplification Primer

<400> SEQUENCE: 7

attcaactcc aggcagcagt ag                                         22


<210> SEQ ID NO 8
<211> LENGTH: 21
<212> TYPE: DNA
<213> ORGANISM: Artificial Sequence
<220> FEATURE:
<223> OTHER INFORMATION: Synthesized Amplification Primer

<400> SEQUENCE: 8

caacctgaag aagagcaaga a                                          21
```

PROTECTION SEQUENCE, PRIMER, PROBE, COMPOSITION AND KIT FOR STEADY-STATE RAPID DETECTION OF NOVEL CORONAVIRUS, AND USE THEREOF AND METHOD THEREFOR

REFERENCE TO AN ELECTRONIC SEQUENCE LISTING

The contents of the electronic sequence listing (Sequence Listing_ST25.txt: Size: 1,932 bytes; and Date of Creation: Dec. 28, 2022) is herein incorporated by reference in its entirety.

TECHNICAL FIELD

The present invention relates to the technical field of in vitro nucleic acid detection, in particular to a protection sequence, primer, probe, composition, kit and method for steady-state quick-acting detection of novel coronavirus and applications thereof.

BACKGROUND OF THE INVENTION

At present, the novel coronavirus epidemic in Europe and the United States is still very serious, threatening the health and life safety of all human beings. According to data released by the World Health Organization, the cumulative number of persons infected by novel coronavirus pneumonia COVID-19 worldwide (as of Apr. 27, 2020) has exceeded 3 million confirmed cases and nearly 190,000 deaths. However, the current nucleic acid test kits for clinical diagnosis of COVID-19 shows a high false negative rate and low sensitivity (positive detection rate is only 30%-50%) due to low sensitivity, resulting in frequent "false negative" detection in patients with high clinical suspicion of COVID-19 infection or "false recovery patients" with low virus latency. The development of COVID-19 detection reagents with high sensitivity and accuracy is the top priority of epidemic prevention and control, and is thus very urgent.

Today, China's National Center for Disease Control and Prevention uses a detection kit of "Variable-temperature Amplification Technology" as a standard for the diagnosis of 2019-nCOV, and the State Food and Drug Administration has approved 15 manufacturers of 2019-nCOV nucleic acid detection products: Beijing Genomics institution (kits), Mgi Tech Co., Ltd. (sequencers), Shanghai ZJ Bio-Tech Co., Ltd. (Liferiver), Shanghai GeneoDx Biotech Co., Ltd., Daan Gene Co., Ltd., SANSURE BIOTECH, Shanghai Biogerm Medical Technology Co., Ltd., and the like. However, many of these enterprises used a set of primers and probes for 2019-nCOV virus published by the National Center for Disease Control and Prevention, and this set of probes and primers has dimer and hairpin structures, which may affect the detection efficiency of the kits. Based on our invention patent technology for the early development of a detection kit for exfoliated cell RNA of cancer subjects, a nucleic acid detection kit for the steady-state quick-acting detection of novel coronavirus SARS-COV-2 is independently developed.

2. The Main Diagnostic Methods and Principles of 2019-nCOV 2019-nCOV may generally be detected by two methods:

2.1. early protein detection (colloidal gold test strip): the colloidal gold test strip is hydrosol of chloroauric acid, which polymerizes into gold particles of a specific size in the presence of a reducing agent, wherein the gold particles can adsorb proteins of the novel coronavirus to achieve detection. The steps of the colloidal gold test strip detection method are summarized as follows: a sample at room temperature is directly added dropwise on the colloidal gold test strip, and whether a positive band appears on the test strip is observed after 10-30 min. The colloidal gold test strip has higher requirements for sample type and concentration of a sample substrate, has low sensitivity and specificity, and can be used for early large-scale screening, but cannot be used as a means of diagnosis for clinical testing.

2.2. Later (constant-temperature or variable-temperature amplification method) nucleic acid detection: at present, the detection kit of "Variable-temperature Amplification Technology" is mainly used in nucleic acid detection as a confirmation standard for 2019-nCOV. Among 7 kits approved by the State Food and Drug Administration, Beijing Genomics institution developed a kit, which used a combined probe-anchored polymerization sequencing method, based on a DNBSEQ-T7 sequencer manufactured by Mgi Tech Co., Ltd., while the other kits all used a fluorescent PCR method. A kit for nucleic acid detection of 2019 novel coronavirus includes two steps: (1) viral nucleic acid extraction. After a sample of body fluid (e.g., a pharyngeal swab or nasal swab) of a patient is collected, virus RNA extraction is performed. (2) Nucleic acid amplification detection. The extracted virus RNA is subjected to real-time quantitative PCR amplification detection, and a "fluorescence signal curve" detected by a PCR instrument allows a laboratory doctor to determine whether the sample is infected with "novel coronavirus".

3. The Current 2019-nCOV Kit has Many Disadvantages:

at present, nucleic acid detection kits for 2019-nCOV approved by China are uneven in quality, and the stability and reliability (sensitivity and specificity) in nucleic acid detection have been questioned. These disadvantages are centrally reflected in two aspects:

(1) low nucleic acid detection rate of 2019-nCOV: news from 21 Century Business Herald on Feb. 2, 2020, "4 tests to confirm?! The production capacity of the kits has gone up, why is it still so difficult to diagnose?", shows the problems that 4 repeats of detection are needed in the current 2019-nCOV epidemic prevention work, etc. It suggests that kits currently used in clinical applications have poor detection sensitivity and specificity. (i) Material were sampled: materials were sampled from pharyngeal swabs for the currently used kits, i.e., obtained from the throat, i.e., the upper respiratory tract, so the virus might not necessarily be obtained effectively because pharyngeal swabs from many patients were negative but the virus exists in lung cell lavage fluid. Therefore, false negative is caused. (ii) The virus is an RNA virus, which may be denatured and degraded after a little longer storage time after the materials are sampled, and thus prone to false negative. (iii) The sensitivity of the kit may still be insufficient, so the virus of low concentration may be suspicious or negative. (iv) Different detection institutions to which our hospital sends samples for detection have different levels, resulting in difference in positive rate. At present, the positive rate of the kits we sent for detection is less than 50%. (v). Many enterprises used a set of primers and probes for the 2019-nCOV virus published by the National Center for Disease Control and Prevention, and laboratory physicians on the front line of epidemic prevention made the following feedback: a standard kit for the diagnosis of 2019-nCOV in the National Center for Disease Control and Prevention had a false negative (with definite clinical symptoms), and we had also noted that this set of primers and probes had a potential "hairpin-like" secondary structure. (vi) Since these newly developed kits were validated with synthetic plasmid fragments or standards, there were no real clinical samples to verify the sensitivity and specificity of the 2019-nCOV kits.

(2) The number of people waiting for nucleic acid detection currently greatly exceeds the detection capacity, which reflects the limitations in two aspects: (i) the detection time is longer: at present, the detection time of the reliable 2019-nCOV nucleic acid detection kit is about 3 hours (including a kit from "Shanghai ZJ Bio-Tech Co., Ltd." in China); and most kits need to perform RNA extraction from samples, which requires more operation steps and is time-consuming, resulting in experiment failure due to the degradation of RNA during the operation. (ii) Due to the infectivity and virulence of the virus, the current 2019-nCOV kit detection is only limited to CDC-accredited laboratories. If the inactivated virus can be effectively treated during sample extraction, the detection of inactivated virus specimens can be extended to testing laboratories of many hospitals, which can greatly improve the detection capacity and shorten the waiting time for nucleic acid detection.

Therefore, it is of great significance to develop high-accuracy and specific detection kits for epidemic prevention and control, in order to overcome the serious problems in the above 2019-nCOV detection.

SUMMARY OF THE INVENTION

In order to solve the problems existing the prior art, the present invention provides a protection sequence, primer, probe, composition, kit and method for steady-state quick-acting detection of novel coronavirus, and applications thereof. According to the present invention, a patient sample is effectively treated by using a lysis/protection solution, the targeted genes of 2019-nCOV virus are released, and a plurality of target gene loci in the lysis/protection solution is effectively identified to form a compound, so that the 2019-nCOV RNA is more stable, and RNA does not need to be extracted and purified. One-step reverse transcription is carried out on the enriched 2019-nCOV RNA compound to obtain cDNA, and the product is recognized by a self-designed 2019-nCOV specific probe, with 40 cycles signals thereof being amplified by a factor of $3.5\times10^{12}$.

The technical solution adopted by the present invention is to provide a protection sequence for steady-state quick-acting detection of novel coronavirus SARS-COV-2, the protection sequence including the following nucleotide sequences:

- protection sequence AP-WHN-1: cctcttctcgttcctcatcacgtagtcgcaacagttcaa (SEQ ID NO: 1);
- protection sequence AP-WHORF1ab-1: gtcctcactgccgtcttgttgaccaacagtttgttgact (SEQ ID NO. 2).

A lysis protection solution for steady-state quick-acting detection of novel coronavirus SARS-COV-2 is provided, the lysis protection solution including 20 nM of the protection sequence AP-WHN-1 and 20 nM of the protection sequence AP-WHORFlab-1 according to claim 1, 1 mmol/L 2-(N-morpholine) ethanesulfonic acid, 100 mmol/L NaCl, 100 mmol/L KCl, 10 mmol/L Tris-HCl, 5 mol/L guanidine hydrochloride, 1% Triton X-100, 0.1 mg/ml proteinase K, and 0.1 mg/ml kieselguhr.

An amplification primer for steady-state quick-acting detection of novel coronavirus SARS-COV-2 is provided, the amplification primer including the following nucleotide sequences:

```
WHN1-F2:
                                    (SEQ ID NO. 3)
5'-CAAGCCTCTTCTCGTTCCT-3';

WHN1-R2:
                                    (SEQ ID NO. 4)
5'-GCAGCAGATTTCTTAGTGACAG-3';
and

WHO1-F2:
                                    (SEQ ID NO. 5)
5'-GCCACTTCTGCTGCTCTTC-3';

WHO1-R2:
                                    (SEQ ID NO. 6)
5'-tgattgtcctcactgccgtc-3'.
```

A primer for steady-state quick-acting detection of novel coronavirus SARS-COV-2 is provided, the probe including the following nucleotide sequences:

```
N probe:
                                    (SEQ ID NO. 7)
5'-FAM-ATTCAACTCCAGGCAGCAGTAG-BHQ1-3';

ORF1ab probe:
                                    (SEQ ID NO. 8)
5'-VIC-CAACCTGAAGAAGAGCAAGAA-MGB-3'
```

A composition for steady-state quick-acting detection of novel coronavirus SARS-COV-2 is provided, the composition including the protection sequence, the amplification primer, and the probe.

A kit for steady-state quick-acting detection of novel coronavirus SARS-COV-2 is provided, the kit including one or more of the protection sequence, the lysis protection solution, the amplification primer, the probe, or the composition.

Applications of a protection sequence, an amplification primer, a probe or a composition as a detection reagent for detection of novel coronavirus SARS-COV-2, wherein the detection reagent is one or more of the protection sequence, the amplification primer, the probe and the composition.

A method for steady-state quick-acting detection of novel coronavirus SARS-COV-2 includes the following steps:

(1) sample treatment: treating the sample with 500 μl of lysis protection solution at 60° C. for 10 min, taking a supernatant onto a column, centrifuging at 12000 rpm for 30 s, and discarding effluent;

(2) rinsing: adding 600 μl of rinsing solution, centrifuging at 12000 rpm for 30 s, and discarding effluent; then adding 400 μl of rinsing solution, centrifuging at 12000 rpm for 45 s, and discarding effluent;

(3) elution: transferring the adsorption column to a new 1.5 ml centrifuge tube, adding 45 μl of eluent, performing heat preservation at 60° C. for 3 min, and centrifuging at 12000 rpm for 2 min;

(4) RT-PCR: taking 8 μl of eluted sample solution after centrifugation, adding 7 μl of NP reaction solution, and then adding 15 μl of PCR reaction solution, and performing detection on a machine; and (5) judgment: performing positive judgment on the resulting CT value to obtain a final detection result.

The present invention has the following beneficial effects: the present invention provides a protection sequence, a primer, a probe, a composition, a kit and a method for steady-state quick-acting detection of novel coronavirus SARS-COV-2, and applications thereof, wherein targeted genes are released through effective treatment on a sample, and an independently-developed novel lysis solution/protection solution can specifically and effectively recognize a plurality of 2019-nCOV target gene loci and form a compound reagent to stabilize 2019-nCOV virus RNA. The development and application of this innovative lysis/protection solution has made this test kit have four major characteristics: high sensitivity (100 times higher initial detection than Shanghai "ZJ Bio-Tech Co., Ltd."), high specificity, high speed (60-70 minutes from sample treatment to results) and dual direct inactivation of the virus to avoid infection of detection personnel. According to the present invention, a patient sample is effectively treated by using a lysis/protection solution, the targeted genes of 2019-nCOV virus are released, and a plurality of target gene loci in the lysis/protection solution is effectively identified to form a compound, so that the 2019-nCOV RNA is more stable, and RNA does not need to be extracted and purified. One-step reverse transcription is carried out on the enriched 2019-nCOV RNA compound to obtain cDNA, and the product is recognized by a self-designed 2019-nCOV specific probe, with its 40 cycles signals being amplified by a factor of $3.5\times10^{12}$.

DETAILED DESCRIPTION OF THE INVENTION

Figure 1:
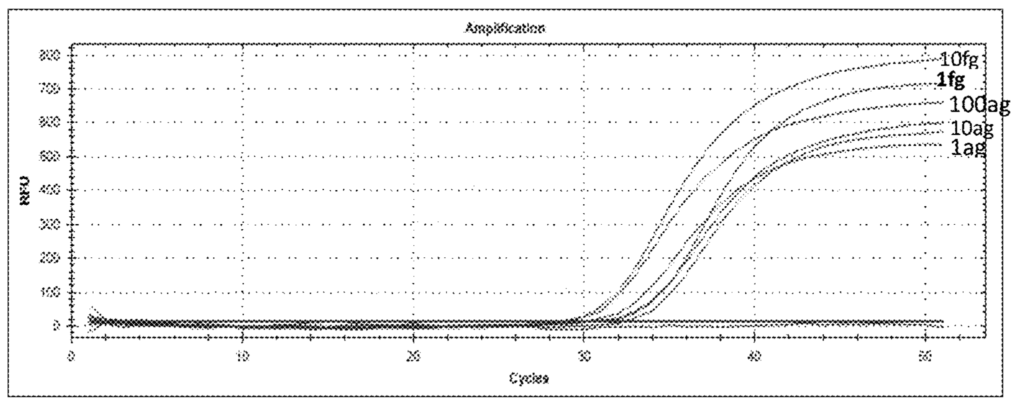
FIG. 1 shows the fluorescence quantitative detection of plasmid cDNA at different concentrations, with a minimum detection copy number of 1 ag (15 copies)/μl.

The experimental methods used in the following examples are conventional methods unless otherwise specified.

(I) Effective Recognition of 2019-nCOV Virus and Protection Effect and Mechanism of Novel Lysis/Protection Solution on Virus RNA.

Primer sequences of new RNA protection sites are designed for a target gene of the novel coronavirus. In addition, a composition ratio, a compound reagent concentration, a salt ion concentration, PH, etc. of various components for lysis/protection in a sample treatment solution are optimized, and a novel lysis solution reaction system is completed to further improve the protection effect of the lysis/protection solution on virus RNA. After the addition of an effective protection agent, a three-dimensional structure of a target protected RNA and the structural allosteric properties of the RNA are clarified, and the effective recognition of 2019-nCOV virus and the protection effect and mechanism of virus RNA in the sample treatment solution in this project kit are studied.

1. The composition ratio of the sample treatment solution is: 1 mmol/L 2-(N-morpholine) ethanesulfonic acid, 100 mmol/L NaCl, 100 mmol/L KCl, 10 mmol/L Tris-HCl, 5 mol/L guanidine hydrochloride, 1% Triton X-100, 0.1 mg/ml proteinase K, and 0.1 mg/ml kieselguhr, as well as 20 nM of a specially designed N gene protection sequence 1 (anchor primer, AP, protection sequence information is detailed in Part II, AP-WHN-1) and 20 nM of a specifically designed ORF1ab1ab protection sequence (AP-WHORF1ab-1, protection sequence information is detailed in Part II).

2. Mechanism of action: first, AP binds to SARS-COV-2 virus RNA to cause local structural changes in RNA, so that the efficiency of binding of RNase to RNA is reduced or the binding position is changed, and RNase cannot cleave and degrade RNA. Secondly, AP first binds efficiently to SARS-COV-2 virus RNA to form a RNA: DNA complex, and such competitive binding reduces RNA exposure areas and prevents RNases from being effectively cleaved. Finally, AP may bind to RNAase to form a complex, and such binding competition inhibits the ability to bind to RNA and affects the RNA activity.

(II) Optimization on Specificity of Primers/Probes: The Specificity of the Kit is Improved, the False Positive Rate is Effectively Reduced, and the Detection Rate is Increased; and with Reference to the Structure of the Novel Coronavirus, Novel Specific Primers/Probes are Designed to Cope with Possible Mutations of the Current Virus.

By designing a probe with dual gene targets of ORF1ab1ab and N genes against the 2019-nCOV virus and performing simultaneous detection, the specificity of the detection of targeted cancer RNA is achieved. The primer design to other regions of ORFlab is added to realize the detection of multiple genes and sites, and effectively increase the detection rate of the kit. Meanwhile, the homology of different types of coronaviruses is analyzed in detail, combined with the latest research results of the 2019 novel coronavirus in structural biology and bioinformatics, to cope with the possible mutations of the 2019 novel coronavirus against a new primer probe designed for its highly conserved region, thereby realizing the immediate update of the detection kit, and ensuring the detection accuracy.

Through bioinformatic analysis, we first designed specific protection sequences for N gene (gene coordinates 2889-2997, FIG. 9A) and ORF1ab1ab gene (gene coordinates 28548-28763, FIG. 8A) of SARS-COV-2, see Ap-WHORF1ab-1 and Ap-WHN-1 in Table 1.

TABLE 1

| Name | Gene coordinates | Detected fragment size (nt) | Protection primer sequence | SEQ ID NO. |
|---|---|---|---|---|
| ORF1ablab | 2889-2997 | 105 | AP-WHORF1ab-1: gtcctcactgccg tcttgttgaccaa cagtttgttgact | SEQ ID NO: 2 |
| N | 28548-28763 | 215 | AP-WHN-1: cctcttctcgttc ctcatcacgtagt cgcaacagttcaa | SEQ ID NO: 1 |

1. Bioinformatic structure prediction of SARS-CoV-2 virus RNA after binding of RNA to AP (FIGS. 8B and 9B), and prediction study of binding of SARS-CoV-2 virus RNA to RNAse (FIGS. 1C and 2C) are performed.

1. Bioinformatic structure prediction of SARS-COV-2 virus RNA after binding of RNA to AP (FIGS. 8B and 9B), and prediction study of binding of SARS-COV-2 virus RNA to RNAse (FIGS. 1C and 2C) are performed.

1) First, we call RPIseq random forest and support vector machine algorithms to evaluate the binding characteristics of the protection sequence to human RNase. By scoring the affinity of RNase RNASE1-7 and a core sequence of N gene (ORFlab gene), it is found that RNASE1, RNASE3, and RNASE7 have a strong binding probability to the core sequence of N gene (ORFlab gene), which may serve as their potential target. catRAPID is called to predict a possible binding position of RNASE1-7 to the core sequence of N gene (ORFlab gene), and it is found that the protection sequence position can interact with RNase.

Figure 8:
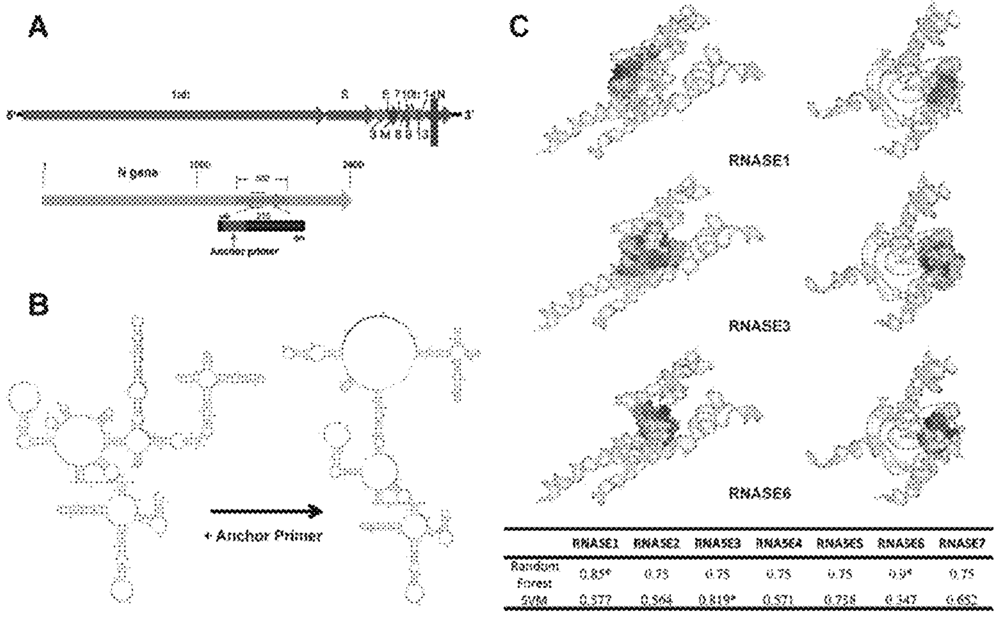
FIG. 8 is a schematic diagram of a secondary structure of a 500 nt fragment of N gene before and after AP binding.
Figure 9:
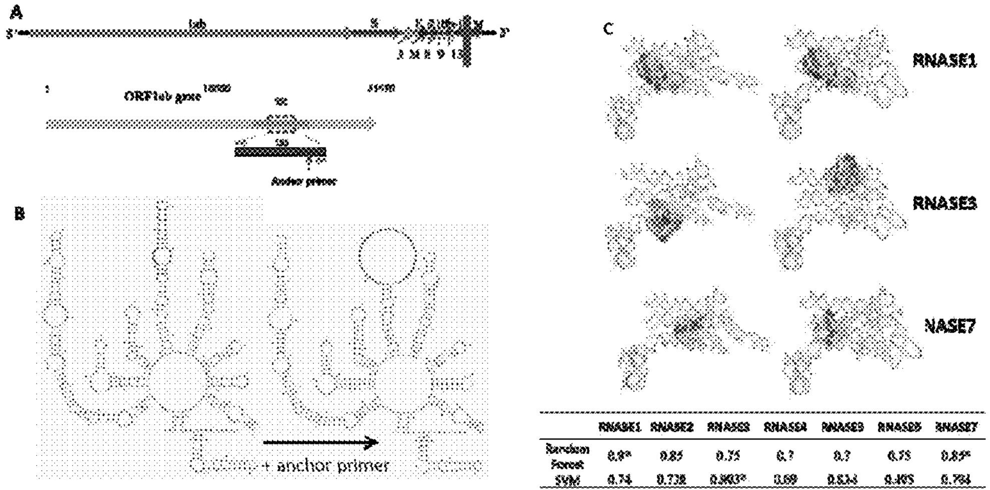
FIG. 9 is a schematic diagram of a secondary structure of a 500 nt fragment of ORF1ab gene before and after AP binding.

Further, a minimum free energy prediction algorithm and RNAstructure are used to predict the RNA secondary structure before and after the binding of the protection sequence to the core sequence of N gene (ORFlab gene) of the virus, respectively. Further, a local alignment algorithm RNAsmc for the RNA secondary structure is used to compare the structural similarity. The results show that the core sequence of N gene (ORFlab gene) RNA before and after the binding to the protection sequence has a structural similarity score of 7.70 (on a scale of 1-10) for N gene and of 9.12 for ORFlab gene, which indicates that the protection sequence has a great influence on the overall structural state of the core sequence of N gene (ORFlab gene). To further validate the effect of primers on N gene (ORFlab gene), a PSMAliven structure alignment tool is used to quantify the effects of the binding region on the RNA structure of the core sequence of N gene (ORFlab gene) (FIGS. 8B and 9B). A PSMAlign result score of 0 indicates no change in structure, on the contrary, the higher the score, the more significant the difference. After calculation, the structural similarity of the core sequence RNA of N gene before and after the binding to the protection sequence is scored as 148 for N gene (18 for ORF1ab gene), which indicates that the protection sequence has a great influence on the structure of N gene. In addition, this result is consistent with an evaluation result on RNAsmc, and the structural changes of the core sequence RNA of N gene (ORFlab gene) may cause abnormal molecular interaction.

2) RNAComposer is further used to predict a 3D structure of the core region of N gene (ORFlab gene), and HDOCK SERVER is used to predict an interaction region of RNase RNASE1-7 and the core sequence of N gene (ORFlab gene) (FIGS. 8C and 9C). The results show that the optimal interaction position of the core sequence of N gene (ORFlab gene) and RNase changes significantly after binding to the protection sequence, which further indicates that the structural changes of the core sequence RNA of N gene (ORFlab gene) may cause abnormal molecular interaction. The results show that RNase 1-7 has a strong probability of binding to the core region of N gene (ORFlab gene), can bind to N gene (ORFlab gene) at the protection sequence, and has a greater impact on the structure of N gene (ORFlab gene) after binding of the protection sequence to N gene (ORFlab gene). In addition, the optimal interaction position of the core sequence of N gene (ORFlab gene) and RNase changes significantly, which indicates that the structural changes of the core sequence RNA of N gene (ORFlab gene) may cause abnormal molecular interaction.

(III) 2019-nCOV Virus is Inactivated by Using the Sample Treatment Solution of the Kit, which is Developed into a Novel RNA Preservation Solution by Studying the Components and Proportioning Process of the Sample Treatment Solution in the Kit; and its Biosafety of the Sample Treatment Solution in Clinical Testing is Investigated.

By improving the compatibility of the sample treatment solution of the kit with the kit, the virus is directly inactivated using a specific reagent, and the effects of its minimum and optimal concentrations on the detection sensitivity and specificity of the kit are investigated. The advantages and disadvantages between the sample treatment solution of this kit and the current RNA preservation solution, e.g., in terms of a preservation time, preservation conditions and preservation effects are compared and analyzed. It is proposed to use the sample treatment solution of this kit for the preservation of clinical pest specimens (viruses, bacteria, etc.), and its inactivation effect on the virus must be clarified. For the 2019 novel coronavirus, the virus inactivation effects are achieved by incubating at 60° C. for 5, 10, 20, and 30 minutes under different temperature conditions, thereby avoiding infection problems of detection personnel.

The sample treatment solution of this kit contains 5 mol/L guanidine hydrochloride, which can destroy the structure of a glycosylated coat protein of SARS-COV-2 virus at room temperature and has an inactivation effect on SARS-COV-virus. This kit has no degradation effect on standard RNA when standard RNA is incubated at 60° C. for 5, 10, 20, and 30 minutes. In addition, this kit has found in clinical tests that RNA of SARS-COV-2 virus can still be extracted after 30 minutes of incubation at 60° C. In this way, this kit has a dual inactivation effect of guanidine salt and 60° C. warm bath (the Guidelines of the National Health Commission has specified that SARS-COV-2 virus can be inactivated at 56° C. for 30 min).

By adding SARS-COV-2 virus plasmid DNA and virus RNA standard to saliva, this kit has a minimum detection sensitivity of 15 copies/ml (cDNA) and 80 copies/ml (RNA standard; the clinical kit has a minimum detection sensitivity of −500 copies/ml at present) respectively, and has higher detection sensitivity.

The test results of this kit in 252 clinically confirmed COVID-19 positive cases show that the kit from Wenzhou Medical University has a better protection effect on RNA integrity under the action of AP of a single gene (N gene), and a high detection rate (80%) can be obtained by means of one-time amplification.

This kit detects the interference of common flora (including *Streptococcus pneumoniae, Streptococcus pyogenes, Klebsiella pneumoniae, Candida albicans, Staphylococcus aureus, Haemophilus influenzae* and *Aspergillus fumigatus*) on a detection system. It is found that common bacteria have no interference effect on the detection of SARS-COV-2 virus RNA.

(IV) the Sample Treatment Technology for the Kit is Further Improved to Realize the Detection of Complex Samples.

The sample treatment solution of this kit can be used to treat a variety of samples, increase the ability of the sample treatment solution to virus lysis and RNA release in complex samples, and improve the protection effect on RNA. Meanwhile, the adaptation conditions of this kit are optimized, the corresponding components in a washing solution are improved to effectively remove the interference of other components in complex samples, and the efficient enrichment of virus RNA is ensured to provide guarantee for subsequent reverse transcription and PCR amplification.

1. This kit can be used to treat a variety of SARS-COV-2 samples, such as nasal swabs, pharyngeal swabs, sputum, urine, feces, conjunctival sac swabs and tears. It is founded in clinical testing:

(5) Primers and Probes of the Kit.

This kit sets a specific protection region for the protection sequence region. SARS-COV-2.

| | | |
|---|---|---|
| N protection sequence | cctcttctcgttcctca tcacgtagtcgcaacag ttcaa | SEQ ID NO: 1 |
| WHN1-F2 | 5'-CAAGCCTCTTCT CGTTCCT-3' | SEQ ID NO: 3 |
| WHN1-R2 | 5'-GCAGCAGATTTCTT AGTGACAG-3' | SEQ ID NO: 4 |
| N-probe | 5'-FAM-ATTCAACTCC AGGCAGCAGTAG-BHQ1-3' | SEQ ID NO: 7 |

| | | |
|---|---|---|
| ORF1ab protection sequence | gtcctcactgccgtc ttgttgaccaacagt ttgttgact | SEQ ID NO: 2 |
| WHO1-F2 | 5'-GCCACTTCTGC TGCTCTTC-3' | SEQ ID NO: 5 |
| WHO1-R2 | 5'-tgattgtcctc actgccgtc-3' | SEQ ID NO: 6 |
| ORF1ab probe | 5'-VIC-CAACCTG AAGAAGAGCAAGA A-MGB-3' | SEQ ID NO: 8 |

| | Site 1 | Site 2 | Site 3 |
|---|---|---|---|
| Total cases | 57 | 115 | 75 |
| Age | 4-79 (52.74) | 1-93 (44.90) | 1-85 (39.74) |
| Sex | Male 31 (54.39%) | Male 58 (50.43%) | Male 38 (50.66%) |
| | Female 26 (45.61%) | Female 57 (49.57%) | Female 37 (49.33%) |
| Specimen type | Sputum 37 (64.91%) | Sputum 38 (33.04%) | Nasal swabs 22 (29.33%) |
| | Pharyngeal swab 10 (17.54%) | Pharyngeal swab 18 (15.65%) | Sputum 11 (14.67%) |
| | Feces 7 (12.28%) | Feces 15 (13.04%) | Pharyngeal 41 (54.67%) |
| | Nasal swab 3 (5.26%) | Sputum/pharyngeal 44 (38.26%) | unknown 1 (1.33%) |
| Detection rate | 70.18% | 80.87% | 78.67% |
| Mean CT value | 31.72 | 27.75 | 32.27 |

2. Treatment of Special Samples:

1) Feces: picking a small amount of sample and put it in the sample treatment solution, incubating at 60° C. for 30 minutes, centrifuging at 12000 rpm for 1 minute, and putting the supernatant onto the column for extraction. This kit can inactivate the virus on the one hand at this step; and effectively lyse the virus to release SARS-COV-2 virus RNA on the other hand, and AP in the sample treatment solution immediately exerts its protection role.

2) Urine: first, centrifuging a collected clinical urine specimen, centrifuging at 12000 rpm for 2 minutes, taking 200-300 μl of urine from the lower layer, and adding 500 μl of sample treatment solution. This step will further concentrate epithelial cells in the urine and degrade all for sample treatment. This step is critical for handling abnormalities in small amount of samples.

Detection Steps:

1. Preparation before the experiment: it is necessary to ensure that experimental facilities are available, and the temperature of a metal bath and a water bath must be calibrated and verified.

2. Sample Treatment

| | |
|---|---|
| 1. Sample treatment* | Treating the sample with a sample treatment solution (about 800 μl) containing a sample at 60° C. for 10 min, putting a supernatant onto a column, centrifuging at 12000 rpm for 30 s, and discarding effluent |
| 2. Rinsing | Adding 60 μl of rinsing solution, centrifuging at 12000 rpm for 30 s, and discarding effluent |
| | Adding 400 μl of rinsing solution, centrifuging at 12000 rpm for 45 s, discarding effluent, and then performing air centrifugation for 2 min to remove residual ethanol |

-continued

| | |
|---|---|
| 3. Elution** | Transferring the adsorption column to a new 1.5 ml centrifuge tube, adding 45 μl of eluent, performing heat preservation at 60° C. for 3 min, and centrifuging at 12000 rpm for 2 min. |
| 4. Reverse transcription | Taking 8 μl of eluted sample solution after centrifugation, adding 7 μl of NP reaction solution, and reacting at 42° C. for 10 min |
| 5. PCR amplification | Adding 15 μl of PCR reaction solution and putting on the machine |

Negative control: $ddH_2O$;

Positive control: 3 μl (full-length plasmid of N gene);

Steps 4 and 5 are performed according to the above treatment procedures.

*Feces specimens need to be centrifuged at 12000 rpm for 1 min, and the supernatant is taken and incubated at 60° C. for 10 min for subsequent experiments.

**Eluant should be treated in a warm bath at 60° C. for 10-15 minutes before use.

3. PCR Amplification

The following procedure is performed on a fluorescent quantitative PCR instrument: setting of cyclic parameters (please refer to instrument operating instructions for setting)

| | Steps | Temperature | Time | Number of cycles |
|---|---|---|---|---|
| 1 | Pre-denaturating | 95° C. | 3 min | 1 |
| 2 | Denaturating | 95° C. | 10 s | 45 cycles |
| | Annealing | 58° C. | 35 s | |

In step 2, fluorescence detection is performed at 58° C. to determine whether fluorophore FAM and quenching group MGB exist, and ROX correction is not selected if there is no MGB option.

*The principle of threshold setting is that a threshold line exceeds a highest point of the negative control and is at the beginning of the exponential amplification period of the positive control.

Quality Control

The quality control procedure is to monitor the detection of negative control and positive control at the same time. The detection result is valid if the negative and positive control results comply with the cases specified by the interpretation of test results.

Interpretation of Test Results:

Negative (−): no Ct value or Ct value≥45

Positive (+): Ct value≤40.

To be reviewed: 40<Ct value<45, and a positive result is determined if Ct value <45 after review again.

(1) Inactivation of Virus Samples

The high-precision novel coronavirus (2019-nCOV) detection kit is based on a development technology of a predecessor cancer early detection kit (RNA detection), and the biosafety risk of collected samples has been technically optimized and improved in the early stage; and on this basis, the compatibility of existing technologies in pharyngeal swabs, nasal secretions and feces has been studied. A reagent is used to treat the sample with guanidine salt, the virus is inactivated after the sample is incubated at 600° C. for 30 minutes, and the subsequent study will shorten the time to 10 minutes.

(2) Detection Stability of Kit

By effectively identifying multiple sites and forming complexes in RNA samples released by cleavage, a triple PCR or multiplex PCR method is used to simultaneously detect multiple gene fragments such as an open reading frame and N gene of coronavirus (2019-nCOV) to avoid the existence of false negative caused by virus mutation. The recognition of RNA sequences in multiple sites protects the RNA integrity, avoids RNA degradation problems caused by sample treatment, and solves the problem of false positive through the optimization of primers and probes, so that the system can determine positive detected at any gene locus of novel coronavirus as positive for initial screening. Multi-target genes are used for protection, and a plurality of gene sequences is detected while the mutation of the virus needs to be considered, thereby preventing missed detection caused by mutation.

Easy degradation of RNA: this kit has released RNA into the sample treatment solution at the same time as the sample acquisition, the sample treatment solution can protect the RNA integrity very effectively while efficiently identifying the released RNA sample at multiple sites and forming complexes, and effective RNA protection is also designed in subsequent detection operations and verified in multiple developed products.

Sensitivity and specificity of the kit: during sample treatment, the RNA sample has been specifically and effectively identified at multiple target gene loci to form a compound, which stably targets novel coronavirus RNA, and multi-target RNA amplification is achieved by selective reverse transcription and enrichment of specific RNA complex; the self-designed primers and probes are significantly superior to probe and primer sequences published by the National Center for Disease Control (bioinformatic analysis has found that no secondary structure such as a hairpin-like structure exists); and by designing primers and probes for dual gene targets of the ORFlab and N genes and detecting both sites at the same time, the sensitivity and specificity of the kit will be greatly improved.

The present invention has the following advantages.

(1) A unique reaction system of innovative lysate and kit: the sample treatment solution can directly store collected virus samples, the sample treatment solution containing guanidine salt which can effectively and rapidly inactivate the virus. At the same time, self-designed materials may also be added to the sample treatment solution, a three-dimensional structure of the target protected RNA and the structural allosteric properties of RNA make the target gene specifically recognized and protected, thereby increasing the sensitivity and specificity of detection.

(2) A unique reaction system of the kit: the combined use of the innovative lysate and reagent makes this detection kit have four characteristics: high sensitivity (100 times higher than Shanghai "ZJ Bio-Tech Co., Ltd."), high specificity, high speed (40-45 minutes from sample preparation to results) and dual direct inactivation of the virus to avoid infection of detection personnel.

(3) Effective treatment of unique sample treatment solution for complex samples (feces and sputum): the sputum sample has been verified in the technology development, the treatment effect on the clinical sample is very satisfactory in the early stage of technology development, and a product, i.e., a lung cancer early detection kit (Guo Xie Zhu Zhun: 20173403247), has been developed using the reagent before optimization. We can apply the existing sample treatment method to clinical applications in samples such as feces.

(4) Rapid sample preparation to detection (40 minutes): the kit currently developed by our team includes four detection steps: release, identification (5 min)—washing (1 min)—elution (2 min)—signal amplification (35 min). Results can be obtained within 45 minutes for pharyngeal swab samples. If used with an automatic nucleic acid extractor, this time can be shortened to 40 minutes.

Conclusion (1) By adding COVID-19 virus plasmid DNA and virus RNA standard to saliva, this kit has a minimum detection sensitivity of 15 copies/ml (cDNA) and 80 copies/ml (RNA standard; the clinical kit has a minimum detection sensitivity of about 500 copies/ml at present) respectively.

(2) The detection results in clinical 252 COVID-19 positive cases show that the kit from Wenzhou Medical University has a better protection effect on RNA integrity (N gene locus), and a high detection rate (80%) can be obtained by means of one-time amplification.

(i) Taizhou Enze Medical Center (57 cases) (CT values need to be re-statistically analyzed): the CT value of ORF gene detected by the extracting solution from "Wenzhou Medical University" is significantly lower than that of an extracting solution from "ZJ Bio-Tech Co., Ltd.", and the detected CT value of ORF gene is decreased by an average of 2.27 cycles, indicating that the sensitivity is improved by about 10 times (p=0.0001 paired with t-test, n=33), while the sensitivities of N gene and E gene are also reduced (p=0.0074 and p=0.6894).

(ii) Wenzhou CDC (59 cases): the CT values of N and E genes detected by extracting solution+amplification solution from "Wenzhou Medical University" are significantly lower than those of other clinical kits (decreased by 3.74 cycles for N gene, p=0.0001; decreased by 2.0 cycles for E gene, p=0.002, n=59);

(ii) Zhejiang CDC (54 cases): the CT values of N and E genes detected by extracting solution+amplification solution from "Wenzhou Medical University" are significantly lower than those of other clinical kits (decreased by 3.79 cycles for N gene, p<0.0001; decreased by XX cycles for E gene, p=0.002, n=59);

(iv) the 1$^{st}$ Affiliated Hospital and 2$^{nd}$ Affiliated Hospital of Wenzhou Medical University (54 mild cases): these cases are detected out by extracting solution from "Wenzhou Medical University"+amplification solution from "ZJ Bio-Tech Co., Ltd.", including 4 cases, accounting for 7.4% (4/54), which become positive again after turning negative;

(v) the 1$^{st}$ Affiliated Hospital of Wenzhou Medical University (11 cases): the detection rate from urine is 36.36% (4/11);

(vi) the positive rate of COVID-19 (N gene) detected by this kit at one time: 70.18% (40/57) in Taizhou; 80.87% (97/115) in Wenzhou CDC: N gene; and 78.67% (59/75) in Zhejiang CDC: N gene. The 2$^{nd}$ Affiliated Hospital of Wenzhou Medical University: 54 cases of clinical mild/ordinary type (turning positive in convalescent phase): 4 cases, 7.4% (4/54).

(3) Therefore, this kit can treat various types of specimens, such as nasal/pharyngeal swabs, sputum, saliva, feces and urine, etc., and trace virus specimens that may exist such as tears and conjunctival sac swabs are being verified.

A detailed progress report is as follows:

(1) Ethics: approved by the ethics committee of Eye Hospital of Wenzhou Medical University.

(2) The COVID-19 pseudovirus cDNA/RNA test indicates that the kit from Wenzhou Medical University has a minimum detection copy number of about 15 copies/ml (for cDNA standard) and 80 copies/ml (for RNA standard), showing higher sensitivity than that of the current clinical kit, and can detect lower viral titers in patient samples and effectively reduce the false negative rate.

2.1. Minimum detection copy number for COVID-19 pseudoviral plasmid cDNA: pseudoviral plasmid cDNA (provided by Xiamen Zeesan Biotech Co., Ltd.) is added to the simulated sample of sputum/saliva, and after the entire lysis/extraction and RT-PCR reaction steps, it is obtained that the minimum copy number of plasmid cDNA of this kit is about 1 ag (15 copies)/μl (FIG. 1) (the current clinical kit has the minimum copy number of about 500 copies/ml).

Figure 2:
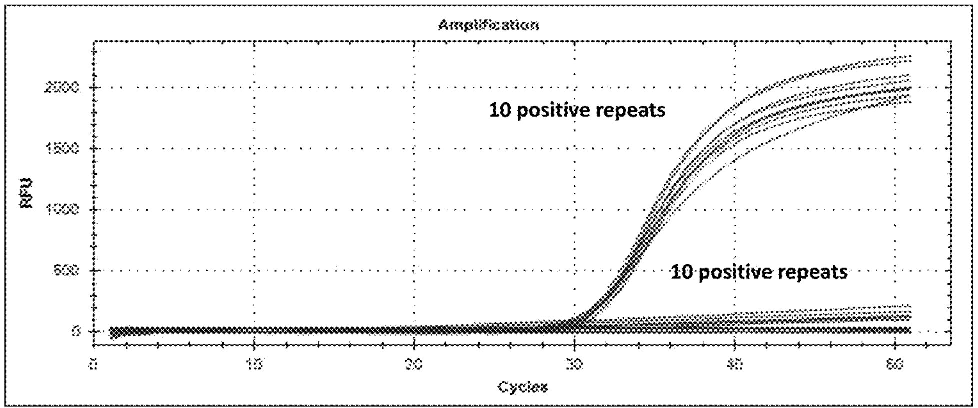
FIG. 2 shows the repeatability detected by virus cDNA: RT-PCR (15 copies/ml), with 10 replicates of 1 ag plasmid DNA and 10 replicates of negative control, without any false positive in 50 cycles of Q-PCR amplification.

2.2. Repeatability of minimum copy number in detection of COVID-19 pseudoviral plasmid cDNA: pseudoviral plasmid DNA having a minimum detection copy number of 15 copies/ml (10 replicate tubes) is added to the simulated sample of sputum/saliva, and after the entire lysis/extraction and RT-PCR reaction steps, this kit has good repeatability in the case of the minimum copy number (FIG. 2).

Figure 3:
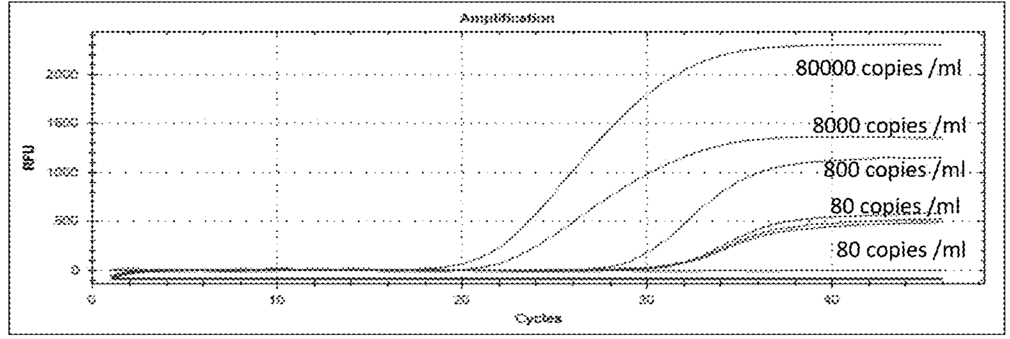
FIG. 3 shows that a minimum detection copy number of a virus RNA standard during RT-PCR detection is 80 copies/ml.
Figure 4:
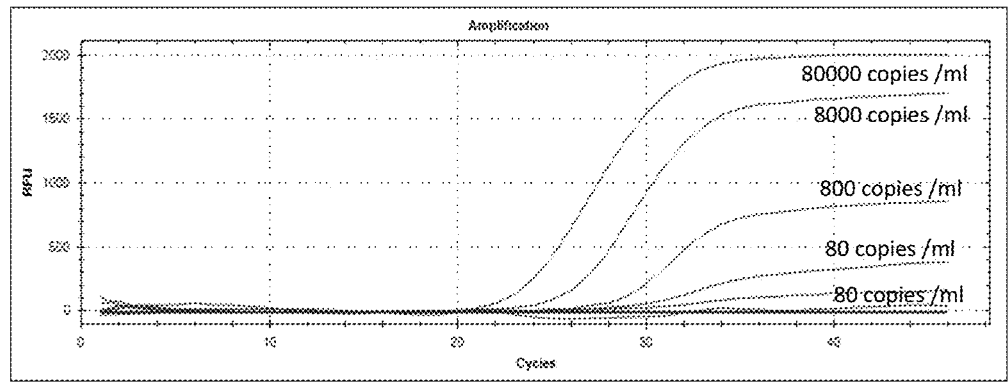
FIG. 4 shows that a minimum detection copy number of a simulated sample of saliva added with the virus RNA standard is 80 copies/ml.
Figure 5:
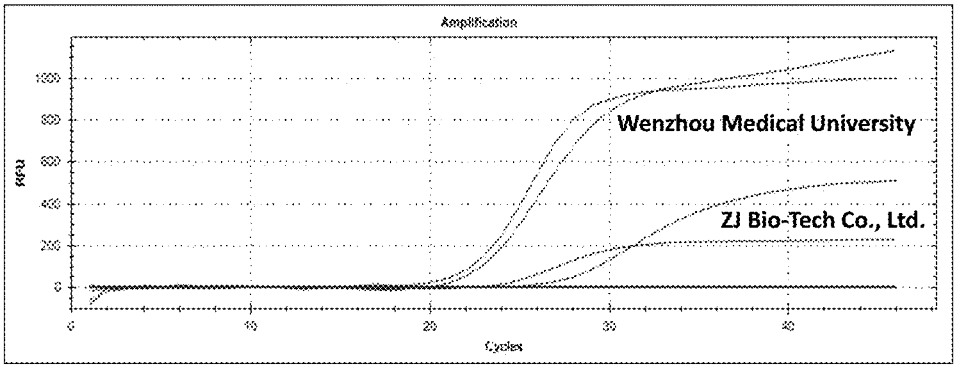
FIG. 5 shows the comparison of a detection effect of a kit produced by "Wenzhou Medical University" and a detection effect of a kit produced by "ZJ Bio-Tech Co., Ltd." as virus RNA standards in saliva samples.
Figure 6:
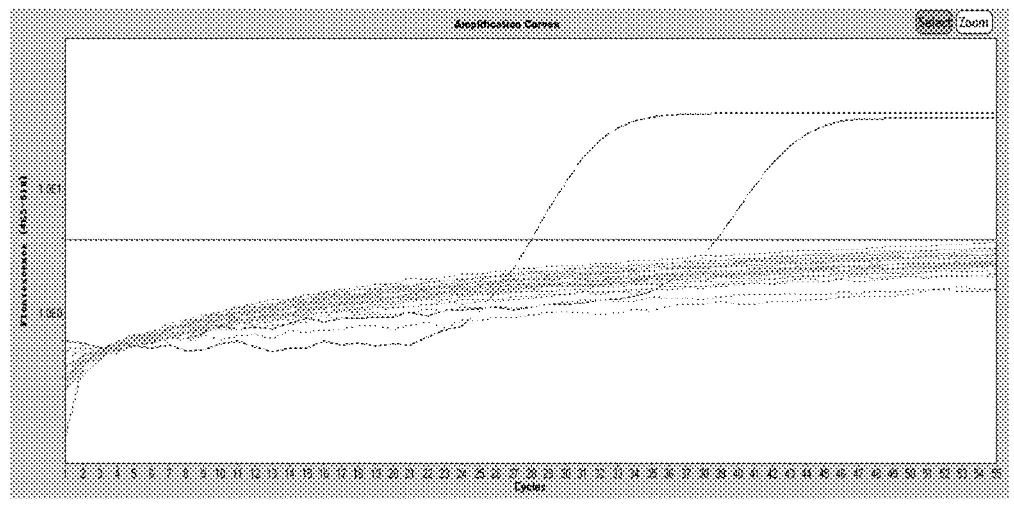
FIG. 6 shows that common bacteria have no interference effect on the detection of COVID-19 virus RNA.

2.3. Verification of the minimum detection copy number in the RT-PCR reaction step with COVID-19 virus RNA standard: the novel coronavirus RNA standard (provided by National Institute of Metrology, China) is added to the simulated samples of the RT-PCR reaction system (FIG. 3) and saliva (FIG. 4), to verify that the minimum detection copy number of the RT-PCR reaction step is 80 copies/ml (about 500 copies/ml for the current clinical kit).

2.4. Parallel comparison studies have found that: 8380 copies/μl of novel coronavirus RNA standard (provided by National Institute of Metrology, China) is added to the simulated sample of sputum/saliva, the RT-PCR reaction steps of the kits from "Wenzhou Medical University" and "ZJ Bio-Tech Co., Ltd." are compared, wherein the CT value detected in "Wenzhou Medical University" is 20, with high intensity of fluorescence signals; and the CT value detected in "ZJ Bio-Tech Co., Ltd." is 26, with low intensity of fluorescence signals.

2.5. Common bacteria have no interference effect on the detection of COVID-19 virus RNA The extracting solution (from Wenzhou Medical University)+RT-PCR amplification system (from ZJ Bio-Tech Co., Ltd.) is applied to detect the interference effects of common flora (including *Streptococcus pneumoniae, Streptococcus pyogenes, Klebsiella pneumoniae, Candida albicans, Staphylococcus aureus, Haemophilus influenzae* and *Aspergillus fumigatus*) on the detection system. The experimental results (3 replicates of nucleic acid extracted from bacteria) show that the expected amplification appears in the strong positive and weak controls (red), while interfering bacteria show no amplification (green).

(3) Statistics of Clinical COVID-19 Patient Sample Collection:

| Participating units | Pharyngeal swab | Nasal swab | Sputum/saliva | Tear/conjunctival sac swab | Urine | Feces/anal swab | Negative | In total |
|---|---|---|---|---|---|---|---|---|
| 1$^{st}$ Affiliated Hospital of Wenzhou Medical University | 0 | 0 | | 43 | 20 | 10 | 0 | 84 |

-continued

| Participating units | Pharyngeal swab | Nasal swab | Sputum/saliva | Tear/conjunctival sac swab | Urine | Feces/anal swab | Negative | In total |
|---|---|---|---|---|---|---|---|---|
| 2nd Affiliated Hospital of Wenzhou Medical University | 6 | 0 | 0 | 11 | 0 | 0 | 70 | 86 |
| Taizhou Enze Medical Center | 10 | 3 | 37 | 0 | 0 | 7 | 0 | 57 |
| Wenzhou Epidemic Disease Prevention and Control Center | 44 | 18 | 38 | 0 | | 15 | 0 | 58 |
| Zhejiang Epidemic Disease Prevention and Control Center | 41 | 22 | 11 | 0 | 0 | 0 | 0 | |
| Eye Hospital of Wenzhou Medical University | 0 | | 0 | 0 | 0 | 0 | 150 | 150 |

3.2. Study on the Effects of Lysis/Protection Solution from Wenzhou Medical University on Stable Protection of COVID-19 Virus RNA In order to detect that the innovative lysis/protection solution can specifically and effectively identify multiple COVID-19 target gene loci and form complexes to stably protect COVID-19 virus RNA, the cooperative unit (Taizhou Enze Hospital) compares the RNA extracted from the lysis/protection solutions from the "Wenzhou Medical University" and "ZJ Bio-Tech Co., Ltd." kits in 33 positive specimens, and the nucleic acid detection kit from "ZJ Bio-Tech Co., Ltd." is used for RT-PCR amplification detection. The results of clinical experiments show that:

(1) The results of clinical experiments show that the positive rate of COVID-19N gene detection is 95%, the positive rate of E gene detection is 100%, and the positive rate of ORF/RDRP gene detection is 100%. This indicates that the kit has a better protection effect on RNA integrity (multiple gene loci) and enables the detection of multiple genes for one-time amplification to improve the detection rate and accuracy of the samples (Table 1).

| Inpatient/outpatient number | Gender | Age | Specimen type | Detection results | Extraction and detection from ZJ | Extraction and detection from WMU |
|---|---|---|---|---|---|---|
| 50151329 | Male | 56 | Sputum | Positive(+) | RDRP26.2932/ E25.83/N26.29 | RDRP 25.79/E 25.85/N 26.7 |
| 50151142 | Male | 75 | Sputum | Positive(+) | RDRP35.21/ 34.45/34.91 | RDRP 37.35/E 0/N 39.57 |
| 50151377 | Female | 67 | Pharyngeal swab | Positive(+) | RDRP38.05/ E37.48/39.02 | RDRP 35.74/E 37.03/N 34.96 |
| 50151088 | Male | 55 | Feces | Positive(+) | RDRP37.68/ E37.09/N38.70 | RDRP 37.65/E 36.94/N 36.8 |
| 50151536 | Female | 77 | Nasopharyngeal swab | Positive(+) | rdrp33.3/E35/N33.07 | RDRP 28.11/E 29.25/N 27.32 |
| 50151345 | Male | 64 | Sputum | Positive(+) | rdrp32.9/E30.3/N38.6 | RDRP 32.87/E 32.7/N 31.86 |
| 50151329 | Male | 56 | Sputum | Positive(+) | RDRP30.38/ E29.53/N30.21 | RDRP 29.47/E 29.12/N 28.46 |

-continued

| Inpatient/outpatient number | Gender | Age | Specimen type | Detection results | Extraction and detection from ZJ | Extraction and detection from WMU |
|---|---|---|---|---|---|---|
| 50151379 | Male | 55 | Nasopharyngeal swab | Positive | RdRP38.97/ E38.9/N37 | RDRP 0/E 39.71/N 37.71 |
| 50151118 | Female | 65 | Nasopharyngeal swab | Positive | RdRP 35.25/E 35.21/N 33.51 | RDRP 35.15/E 34.33/N 33.95 |
| 50151406 | Male | 33 | Sputum | Positive(+) | rdrp35.6/E34.6/N33.5 | RDRP 31.58/E 32.11/N 30.69 |
| 50150887 | Male | 34 | Sputum | Positive | RDRP33.9/ E29.9/N 30.8 | RDRP 32.81/E 32.58/N 32.3 |
| 50151409 | Female | 51 | Sputum | To be reviewed | E36, N35.9 | RDRP 0/E 36.29/N 43.69 |
| 50150812 | Male | 50 | Sputum | Positive(+) | rdrp37.4/E35.5/N35 | RDRP 35.07/E 34.2/N 33.9 |
| 50151541 | Female | 48 | Sputum | Positive(+) | rdrp36.99/E35.6/N35.6 | RDRP 0/E 0/N 35.14 |
| 50151270 | Female | 44 | Pharyngeal swab | Positive | RDRP 35.22/E31.68/N 32.97 | RDRP 35.15/E 32.35/N 31.75 |
| 50151536 | Female | 77 | Sputum | Positive(+) | RDRP29.8/E28.0/E29.2 | RDRP 21.43/E 22.17/N 23.09 |
| 50151307 | Female | 68 | Sputum | To be reviewed | E37.9/N38.7 | RDRP 31.38/E 31.94/N 31.83 |
| 50150765 | Female | 56 | Sputum | Positive(+) | RDRP35.6/E32.7/N33.3 | RDRP 35.26/E 34.32/N 33.9 |
| 50151436 | Female | 30 | Sputum | Positive(+) | RDRP37.46/E34.5/N36.36 | RDRP 35.25/E 34.54/N 34.06 |
| 50150798 | Male | 43 | Sputum | Positive(+) | rdrp36.34/E33.1/N33.03 | RDRP 37.03/E 34.43/N 35.89 |
| 50151142 | Male | 75 | Sputum | Positive(+) | RDRP38.66/E35.7/N37.5 | RDRP 38.95/E 39.82/N 28.03 |
| 50151345 | Male | 64 | Sputum | Positive(+) | rdrp34.91/E33.9/N32.53 | RDRP 37.08/E 37.22/N 36.98 |
| 9000548489 | Female | 43 | Pharyngeal swab | Negative | RdRP 41.7/E 36.56/N 36.9 | RDRP 35.91/E 35.84/N 36.04 |
| 50150798 | Male | 43 | Pharyngeal swab | Positive | RdRP38.30/E 38.14/N 35.78 | Non-standard curve |
| 50151020 | Female | 26 | Pharyngeal swab | Positive(+) | RdRP 38.79/E 37.07/N 37.71 | RDRP 33.87/E 34.02/N 34.27 |
| 50150887 | Male | 34 | Pharyngeal swab | Positive(+) | RdRP 31.61/E 28.56/N 28.78 | RDRP 28.86/E 28.92/N 28.44 |
| 50151237 | Male | 70 | Pharyngeal swab | Positive | RDRP38.01/E35.94/N35.38 | RDRP 33.6/E 35.07/N 34.09 |

-continued

| Inpatient/outpatient number | Gender | Age | Specimen type | Detection results | Extraction and detection from ZJ | Extraction and detection from WMU |
|---|---|---|---|---|---|---|
| 50151166 | Male | 44 | Pharyngeal swab | Positive | RdRP 32.53/E 31.16/N 35.41 | RDRP 33.74/E 33.65/N 33.64 |
| 50151065 | Male | 51 | Sputum | Positive(+) | RDRP37.70/E37.12/N37.94 | RDRP 29.08/E 28.45/N 28.47 |
| 50150954 | Female | 41 | Pharyngeal swab | Positive | RdRP 33.77/E 32.98/N39.01 | RDRP 32.3/E 32.56/N 32.68 |
| 50151017 | Male | 38 | Pharyngeal swab | Positive | RdRP 39.91/E 39.93/N38.21 | Non-standard curve |
| 50151406 | Male | 33 | Faeces | Positive | RDRP33.12/E30.88/N32.29 | RDRP 23.98/E 25.39/N 24.04 |
| 50151406 | Male | 33 | Sputum | Positive | RDRP35.53/E32.72/N34.12 | Non-standard curve |

Figure 7:
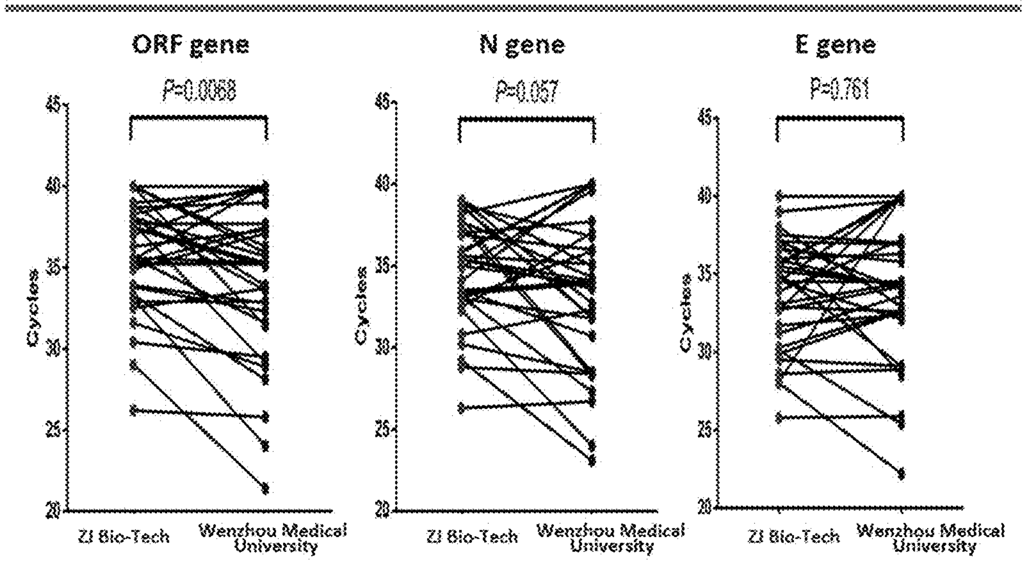
FIG. 7 shows that the CT value of ORF gene detected by an extracting solution of "Wenzhou Medical University" is lower than that of "ZJ Bio-Tech Co., Ltd.".

(2) The CT values of three gene fragments (ORF, E and N) detected by the extracting solutions from "Wenzhou Medical University" and "ZJ Bio-Tech Co., Ltd." are compared. The results show that the CT value of the ORF gene detected by the extracting solution from "Wenzhou Medical University" is significantly lower than that of the extracting solution from "ZJ Bio-Tech Co., Ltd." (p=0.0067, N gene, p=0.057; E gene, p=0.761, paired with t-test, n=33, see FIG. 7), the CT value of the ORF gene is reduced by an average of 3 cycles, and the copy number of detected COVID-19RNA by pseudoviral standard curve conversion is increased by about 10 times.

3.4. Clinical Compliance Rate (vi) The positive rate of COVID-19 (N gene) detected by this kit at one time: 70.18% (40/57) in Taizhou; 80.87% (97/115) in Wenzhou CDC: N gene; and 78.67% (59/75) in Zhejiang CDC: N gene. The 1st Affiliated Hospital of Wenzhou Medical University: 54 cases of clinical mild/ordinary type (turning positive in convalescent phase): 4 cases, 7.4% (4/54). 3.5. The extracting solution from "Wenzhou Medical University" can treat a variety of complex COVID-19 patient samples:

| Participating units | Pharyngeal swab | Nasal swab | Sputum/saliva | Tear/conjunctival sac swab | Urine | Feces/anal swab | Negative | In total |
|---|---|---|---|---|---|---|---|---|
| 1st Affiliated Hospital of Wenzhou Medical University | 0 | 0 | | 43 | 20 | 10 | 0 | 84 |
| 2nd Affiliated Hospital of Wenzhou Medical University | 6 | 0 | 0 | 11 | 0 | 0 | 70 | 86 |
| Taizhou Enze Medical Center | 10 | 3 | 37 | 0 | 0 | 7 | 0 | 57 |
| Wenzhou Epidemic Disease Prevention and Control Center | 44 | 18 | 38 | 0 | | 15 | 0 | 58 |
| Zhejiang Epidemic Disease Prevention and Control Center | 41 | 22 | 11 | 0 | 0 | 0 | 0 | |
| Eye Hospital of Wenzhou Medical University | 0 | | 0 | 0 | 0 | 0 | 150 | 150 |

3.6. COVID-19 Virus Inactivation and Safety

The sample treatment solution of this kit contains guanidine salt, which has an inactivation effect on the virus (which has been confirmed in existing reports). In addition, the sample treatment stage can achieve an effect of inactivation of the virus at 60° C. for 30 min. Virus inactivation can effectively reduce the exposure risk of detection personnel, protect the safety of operators, and reduce the risk of infection in testing laboratories.

3.7. Rapid Sample Preparation to Detection (40 Min):

This kit includes four detection steps: release, identification (5 min)—washing (1 min)—elution (2 min)—signal amplification (35 min). Results can be obtained within 45 minutes for pharyngeal swab samples. If used with an automatic nucleic acid extractor, this time can be shortened to 40 minutes.

3.8. Detection Sensitivity

By adding COVID-19 virus plasmid DNA and virus RNA standards, it is found in ex vivo experiments that this kit has the minimum detection sensitivities of 15 copies/ml (cDNA) and 80 copies/ml, respectively, with a low detection line. In addition, clinical detection in 1st Affiliated Hospital and 2nd Affiliated Hospital of Wenzhou Medical University has found that among 54 patients recovering from COVID-19, there are patients who are positive after turning negative clinically. Therefore, this kit has high detection sensitivity.

The materials, reagents, etc. used in the following examples unless otherwise specified, may be obtained commercially.

Notes to technical personnel: although the present invention has been described in accordance with the above specific examples, the inventive idea of the present invention is not limited to the present invention, and any modification using the idea of the present invention will be included in the protection scope of this patent.

The above is only preferred examples of the present invention, the protection scope of the present invention is not limited to the above examples, all technical solutions belonging to the ideas of the present invention are within the protection scope of the present invention. It should be noted that those of ordinary skill in the art may also make several improvements and modifications without departing from the principles of the present invention, which should be considered as the protection scope of the present invention.

The invention claimed is:

1. A composition comprising the following nucleotide sequences: SEQ ID NO: 1 and SEQ ID NO: 2.

2. A lysis protection solution for detection of coronavirus SARS-COV-2, comprising 20 nM of the nucleotide sequence of SEQ ID NO: 1 and 20 nM of the nucleotide sequence of SEQ ID NO: 2, 1 mmol/L 2-(N-morpholine) ethanesulfonic acid, 100 mmol/L NaCl, 100 mmol/L KCl, 10 mmol/L Tris-HCl, 5 mol/L guanidine hydrochloride, 1% Triton X-100, 0.1 mg/ml proteinase K, and 0.1 mg/ml kieselguhr.

3. A composition comprising amplification primer pairs for detection of coronavirus SARS-CoV-2, comprising the following nucleotide sequences:

WHN1-F2: SEQ ID NO: 3;

WHN1-R2: SEQ ID NO: 4 and

WHO1-F2: SEQ ID NO: 5;

WHO1-R2: SEQ ID NO: 6.

4. A composition for detection of coronavirus SARS-COV-2, comprising:

the composition of claim 1; and amplification primer pairs comprising the following nucleotide sequences:

WHN1-F2: SEQ ID NO: 3;

WHN1-R2: SEQ ID NO: 4 and

WHO1-F2: SEQ ID NO: 5;

WHO1-R2: SEQ ID NO: 6; and at least one probe selected from the group consisting of:

N probe: 5'-FAM-SEQ ID NO: 7-BHQ1-3; and

ORF lab probe: 5'-VIC-SEQ ID NO: 8-MGB-3'.

5. A kit for detection of coronavirus SARS-COV-2, comprising the nucleotide sequences of SEQ ID NO: 1 and SEQ ID NO: 2, and amplification primer pairs, comprising the following nucleotide sequences:

WHN1-F2: SEQ ID NO: 3;

the WHN1-R2: SEQ ID NO: 4.

6. The kit according to claim 5, further comprising at least one probe for detection of coronavirus SARS-COV-2, selected from the group consisting of:

N probe: 5'-FAM-SEQ ID NO: 7-BHQ1-3'; and

ORF lab probe: 5'-VIC-SEQ ID NO: 8-MGB-3'.

7. A method for detecting a coronavirus SARS-COV-2, wherein the method comprises treating a sample, suspected of having a coronavirus SARS-COV-2, with a detection reagent comprising the composition of claim 4, and performing RT-PCR on the treated sample in order to detect a coronavirus SARS-COV-2.

* * * * *